United States Patent
Ohta et al.

(10) Patent No.: US 11,702,636 B2
(45) Date of Patent: Jul. 18, 2023

(54) COMPOSITION INDUCING CELL REPROGRAMMING AND PRODUCTION METHOD FOR MULTIFUNCTION CELLS USING SAID COMPOSITION

(71) Applicant: NATIONAL UNIVERSITY CORPORATION KUMAMOTO UNIVERSITY, Kumamoto (JP)

(72) Inventors: Kunimasa Ohta, Kumamoto (JP); Naofumi Ito, Kumamoto (JP)

(73) Assignee: National University Corporation Kumamoto University, Kumamoto (JP)

(*) Notice: Subject to any disclaimer, the term of this patent is extended or adjusted under 35 U.S.C. 154(b) by 545 days.

(21) Appl. No.: 15/776,350

(22) PCT Filed: Nov. 15, 2016

(86) PCT No.: PCT/JP2016/083874
§ 371 (c)(1),
(2) Date: May 15, 2018

(87) PCT Pub. No.: WO2017/086329
PCT Pub. Date: May 26, 2017

(65) Prior Publication Data
US 2020/0255805 A1 Aug. 13, 2020

(30) Foreign Application Priority Data
Nov. 16, 2015 (JP) ................. 2015-223656

(51) Int. Cl.
*C12N 5/077* (2010.01)
(52) U.S. Cl.
CPC ...... *C12N 5/0652* (2013.01); *C12N 2501/998* (2013.01); *C12N 2502/1323* (2013.01)
(58) Field of Classification Search
None
See application file for complete search history.

(56) References Cited

U.S. PATENT DOCUMENTS

| | | |
|---|---|---|
| 9,587,224 B2 | 3/2017 | Ohta |
| 2006/0222636 A1 | 10/2006 | Rambukkana |
| 2008/0193470 A1 | 8/2008 | Masignani et al. |
| 2014/0255942 A1 | 9/2014 | Ohta |
| 2014/0356389 A1 | 12/2014 | Masignani et al. |
| 2017/0360833 A1 | 12/2017 | Ohta et al. |

FOREIGN PATENT DOCUMENTS

| | | | | |
|---|---|---|---|---|
| EP | 0765667 A1 * | 4/1997 | ............ | A61P 37/04 |
| EP | 0765667 A1 | 4/1997 | | |
| EP | 2733204 A1 | 5/2014 | | |
| EP | 3144384 A1 | 3/2017 | | |
| JP | 2008-529558 | 8/2008 | | |
| WO | WO-2011008867 A1 * | 1/2011 | ............ | C12P 21/02 |
| WO | 2013008803 A1 | 1/2013 | | |
| WO | 2014167943 A1 | 10/2014 | | |
| WO | 2015174364 A1 | 11/2015 | | |

OTHER PUBLICATIONS

Ohta (PLoS ONE, 7:e51866, 2012) (Year: 2012).*
Li et al, 2014 (Journal of Hematology & Oncology, 7:50, p. 1-18) (Year: 2014).*
Sommer et al., 2013 (J. Cell. Physiol., vol. 228, p. 267-275) (Year: 2013).*
Zhang et al., 2012 (Cell Cycle, vol. 11, No. 24, p. 1-9) (Year: 2012).*
Ohta, Kunimasa et al., "Lactic Acid Bacteria Convert human Fibroblasts to multipotent Cells" Plos One, vol. 7, Issue 12, Dec. 2012, pp. 1-10.
International Search Report dated Feb. 14, 2017 for International Application No. PCT/JP2016/083874.
International Preliminary Report on Patentability for PCT/JP2016/083874.
Extended European Search report dated Apr. 26, 2019 for European Patent application No. 16866330.0.
Ma, Tianhua et al., "Progress in the Reprogramming of Somatic Cells" Circulation Research, vol. 112, No. 3, pp. 1-14, Feb. 1, 2013.
Ito, Naofumi et al., "Reprogramming of human somatic cells by bacteria" Development Growth and Differentiation, vol. 57, No. 4, pp. 1-8, Apr. 10, 2015.
Yenamandra, Sp et al., "Stem cell gene Expression in MRS18-2-Immortalized rat Embryonic fibroblasts" Cell Death & Disease, vol. 3, No. 1, pgs. Jan. 1, 2012.
Kashuba, Elena et al., "MRPS18-2 Protein Immortalizes primary rat embryonic fibroblasts and endows them with stem cell-like properties" PNAS, vol. 106, No. 47, pp. 19866-19871, Nov. 24, 2009.
Wang, Min et al., "RPS2: A novel Therapeutic target in Prostate cancer" Journal of Experimental & Clinical Cancer Research, Biomed Central Ltd, London UK, vol. 28, No. 1, pp. 1-12, Jan. 12, 2009.
Zhou, Xiang et al., "Ribosomal Proteins: Functions beyond in Ribosome" Journal of Molecular Cell Biology, vol. 7, No. 2, pp. 92-104, Apr. 1, 2015.

(Continued)

*Primary Examiner* — Emily A Cordas
(74) *Attorney, Agent, or Firm* — Hunton Andrews Kurth LLP

(57) ABSTRACT

An exemplary composition can be provided which includes an identified substance that induced cell reprogramming. Cells can also be provided having pluripotency having high safety when applied to regenerative medicine, using the composition, and a production method therefor. A cell reprogramming-inducing composition can include at least one 30S ribosome protein selected from the group consisting of 30S ribosome protein S2, 30S ribosome protein S8 and 30S ribosome protein S15 as a substance that reprograms cells derived from a mammalian animal is provided. Further, an exemplary production method for cells having pluripotency from somatic cells using the composition can be provided.

5 Claims, 1 Drawing Sheet
Specification includes a Sequence Listing.

(56) References Cited

OTHER PUBLICATIONS

Ito, Naofumi et al., "Ribosome Incorporation into Somatic Cells Promotes Lineage Transdifferentiation towards Multipotency" Scientific Reports, vol. 8, No. 1, pp. 1-14, Jan. 26, 2018.

Reason for Refusal dated Oct. 27, 2020 for Japanese patent application No. JP2017-551898 and English-language translation (machine version) thereof.

* cited by examiner

COMPOSITION INDUCING CELL REPROGRAMMING AND PRODUCTION METHOD FOR MULTIFUNCTION CELLS USING SAID COMPOSITION

CROSS REFERENCE TO RELATED APPLICATION(S)

This application relates to, and claims the benefit and priority from International Patent Application No. PCT/JP2016/083874 filed Nov. 15, 2016 that published as International Patent Publication No. WO 2017/086329 on May 26, 2017, which claims the benefit and priority from Japanese Patent Application No. JP2015-223656 filed Nov. 16, 2015, the entire disclosures of which are incorporated herein by reference in their entireties.

FIELD OF THE DISCLOSURE

The present disclosure relates to a composition for inducing reprogramming of cells and to a method for producing cells having pluripotency by inducing reprogramming of cells using the composition.

BACKGROUND INFORMATION

ES cells and iPS cells have been developed as cells having an ability to change into various kinds of cells (pluripotency). With ES cells, however, there is an ethical problem of using fertilized ova. There is also an problem that when differentiated cells or organs prepared from ES cells are transplanted into a patient, the immune system may recognize them as non-self and attack them. Although iPS cells can solve these problems for ES cells, on the other hand, technologies for standardizing iPS cells are still under development and additionally, the problem of canceration of cells cannot be completely eliminated.

As a method of producing embryonic stem (ES) cell-like cells, a reprogramming method using *Mycobacterium Repurae*, a leprae fungi or the components thereof has been proposed (see, e.g., U.S. Patent Publication No. 2006/0222636).

In addition, the present inventors have also proposed a method for producing cells having pluripotency from somatic cells by infecting somatic cells with lactic acid bacteria or *Bacillus subtilis* natto (see, e.g., International Patent Publication WO 2013/008803, and Ohta et al., PLoS ONE 7(12):e51866, 2012) or a method of producing cells having pluripotency by bringing protein components having a molecular weight of more than 100 kDa into contact with somatic cells (see, e.g., International Patent Publication WO 2014/167943).

SUMMARY OF EXEMPLARY EMBODIMENTS

One of the objects of the present disclosure is to provide a composition comprising an identified substance which induces reprogramming of cells. Further, another object of the present disclosure is to provide cells having pluripotency cell with high safety in application to regenerative medicine using the composition and a method for producing the same.

For example, a specific 30S ribosomal protein, which is a ribosome constituent, can reprogram human skin cells having finished cell differentiation and form cell clusters like ES cells or iPS cells, effectuation the exemplary embodiment(s) of the present disclosure.

To that end, the following exemplary embodiments of the present disclosure are provided, as follows:

[1] A composition for inducing reprogramming of cells, comprising at least one 30S ribosomal protein selected from the group consisting of 30S ribosomal protein S2, 30S ribosomal protein S8 and 30S ribosomal protein S15 as a substance for reprogramming cells derived from mammals (for example, human or mouse).

[2] The composition according to exemplary embodiment [1], wherein the 30S ribosomal protein S2, the 30S ribosomal protein S8 and the 30S ribosomal protein S15 are isolated and purified 30S ribosomal protein S2, isolated and purified 30S ribosomal protein S8 and isolated and purified 30S ribosomal protein S15.

[3] The composition according to exemplary embodiment(s) [1] or [2], comprising 30S ribosomal protein S2 as a substance for reprogramming cells.

[4] The composition according to any one of exemplary embodiment(s) [1] to [3], where the cell derived from mammals is a human-derived skin cell or cancer cell.

[5] The composition according to any one of exemplary embodiment(s) [1] to [4], where the 30S ribosomal protein is a recombinant protein.

[6] A method for inducing reprogramming of somatic cells (which are in body or isolated) derived from mammals (for example, human or mouse) by bringing at least one 30S ribosomal protein selected from the group consisting of 30S ribosomal protein S2, 30S ribosomal protein S8 and 30S ribosomal protein S15 into contact with the somatic cells.

[7] The method according to exemplary embodiment [6], where the 30S ribosomal protein S2, the 30S ribosomal protein S8 and the 30S ribosomal protein S15 are isolated and purified 30S ribosomal protein S2, isolated and purified 30S ribosomal protein S8 and isolated and purified 30S ribosomal protein S15.

[8] The method according to exemplary embodiment(s) [6] or [7], where cells are brought into contact with 30S ribosomal protein S2.

[9] The method according to any one of exemplary embodiment(s) [6] to [8], where the somatic cell is a human-derived cell.

[10] The method according to any one of exemplary embodiment(s) [6] to [9], where the 30S ribosomal protein is a recombinant protein.

[11] A cell having pluripotency produced by the method according to any one of exemplary embodiment(s) [6] to [10].

[12] A medium for producing cells having pluripotency from isolated mammal-derived somatic cells, comprising at least one 30S ribosomal protein selected from the group consisting of 30S ribosomal protein S2, 30S ribosomal protein S8 and 30S ribosomal protein S15.

[13] The medium according to exemplary embodiment(s) [12], where the 30S ribosomal protein S2, the 30S ribosomal protein S8 and the 30S ribosomal protein S15 are isolated and purified 30S ribosomal protein S2, isolated and purified 30S ribosomal protein S8 and isolated and purified 30S ribosomal protein S5.

[14] The medium according to exemplary embodiment(s) [12] or [13], comprising 30S ribosomal protein S2.

[15] The medium according to any one of exemplary embodiment(s) [12] to [14], where the 30S ribosomal protein is a recombinant protein.

[16] A medium kit comprising the composition according to any one of exemplary embodiment(s) [1] to [5] and an animal cell culturing medium.

Exemplary embodiments of the present disclosure can reprogram somatic cells without using introduction of a gene into somatic cells and forced expression thereof.

The aspects described above and further aspects, features and advantages of the present disclosure may also be found in the exemplary embodiments which are described in the following with reference to the appended drawings and claims.

BRIEF DESCRIPTION OF THE DRAWINGS

Further exemplary embodiments of the present disclosure are detailed in the description of the Figures, where this description shall not limit the scope of the present disclosure. The Figures show that.

Figure 1:
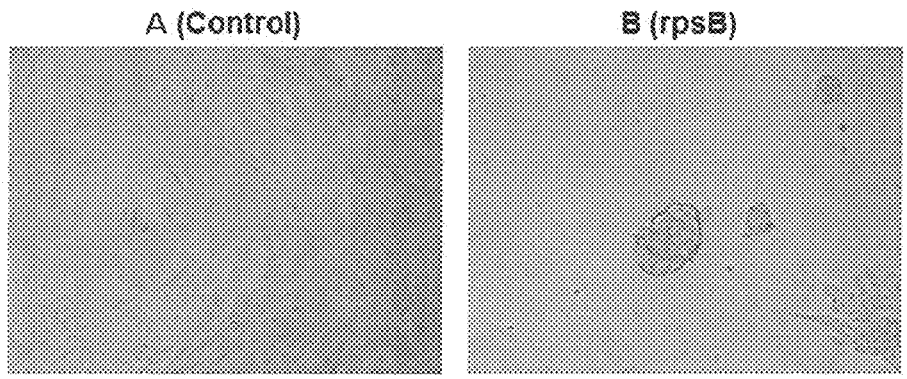
FIG. 1A an illustration of HDF cells cultured together with purified 30S ribosomal protein S2 prepared in Example 4 (3 days after culturing), whereas HDF cells are shown as a control.
FIG. 1B is an illustration of HDF cells cultured together with the purified 30S ribosomal protein S2 prepared in Example 4 (3 days after culturing), whereas HDF cells are shown as cell clusters induced by the RpsB protein.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

Hereinafter, the present disclosure will be illustrated and described in detail with reference to the exemplary embodiments, along with the exemplary methods and materials which can be used in practice of the present disclosure.

Unless otherwise specified in the text, various technical terms and scientific terms used in present specification have the same meaning as commonly understood by one of ordinary skill in the art to which the present disclosure belongs. Additionally, any materials and methods equivalent or similar to those described in present specification can be used as well in the practice of the present disclosure.

Further, all publications and patents referenced in the present application constitute a part of present specification, for example, as referring to methods and materials and the like that can be used in the present disclosure, and are thus incorporated herein by reference in their entireties.

In the present disclosure, the term "inducing reprogramming of cells" can denote as transform somatic cells or cancer cells of mammals, for example, epithelial cells into cells having pluripotency and an ability of differentiating into various cells like ES cells and iPS cells by bringing the cells into contact with a composition containing at least one 30S ribosomal protein selected from the group consisting of 30S ribosomal protein S2, 30S ribosomal protein S8 and 30S ribosomal protein S15 as a substance inducing reprogramming. In this exemplary context, the term contact means that cells are placed in a condition wherein the cells can come into contact with any of or some of or all of the above-described 30S ribosomal proteins, and its embodiment is not particularly restricted, however, in an exemplary condition, the above-described 30S ribosomal proteins are allowed to present in an environment wherein somatic cells survive (for example, medium) and they can act on the somatic cells.

S2, S8 and S15 ribosomal proteins, which can be used in the present invention, are three of 21 kinds of ribosomal proteins constituting the 30S subunit of the ribosome. 30S ribosomal protein S2 that can be used in the present invention is a protein composed of an amino acid sequence shown in SEQ ID NO: 1. 30S ribosomal protein S8 that can be used in the present invention is a protein composed of an amino acid sequence shown in SEQ ID NO: 2. 30S ribosomal protein S15 that can be used in the present invention is a protein composed of an amino acid sequence shown in SEQ ID NO: 3. The ribosomal protein that can be used in the present invention can be produced, for example, by transfecting DNA coding an amino acid sequence of 30S ribosomal protein S2, 30S ribosomal protein S8 or 30S ribosomal protein S15 into a host such as *E. coli* and the like and expressing the DNA using a genetic modification technique. Furthermore, the expressed ribosomal protein can be isolated and purified using known techniques.

30S ribosomal protein that can be used in the exemplary embodiment of the present disclosure can also contain one having substitution, deletion or mutation of some amino acids of a protein composed of an amino acid sequence shown in SEQ ID NO: 1, SEQ ID NO: 2 or SEQ ID NO: 3 and having reprogramming induction activity. Such exemplary protein can be produced by making a partially modified or changed DNA of a DNA sequence coding an amino acid sequence of 30S ribosomal protein S2, 30S ribosomal protein S8 or 30S ribosomal protein S15, and transfecting the DNA into a host such as *E. coli* and the like and expressing it using a genetic modification technique. Such a technique is well known and the technique can be changed appropriately in the production. Specifically, it denotes a protein having 80% or more, preferably 90% or more, more preferably 95% or more, further preferably 98% or more, particularly preferably 99% or more identity with an amino acid sequence shown in SEQ ID NO: 1, SEQ ID NO: 2 or SEQ ID NO: 3 and having cell reprogramming induction activity. The cell reprogramming induction activity can be confirmed, for example, by the same method as shown in examples of the present invention, using such a protein. The 30S ribosomal protein that can be used in the present invention is preferably 30S ribosomal protein S2.

In the present disclosure, "comprising/containing 30 ribosomal protein S2" can mean containing 30 ribosomal protein S2 as a single protein molecule, and/or can be meant to, e.g., exclude a case containing it as a part of the 30S ribosome itself. The same can apply also to 30 ribosomal protein S8 and 30 ribosomal protein S15.

In contact of a composition containing at least one 30S ribosomal protein selected from the group consisting of 30S ribosomal protein S2, 30S ribosomal protein S8 and 30S ribosomal protein S15 (hereinafter, which can be referred to, e.g., as "30S ribosomal protein" unless otherwise stated or unless stated separately in the context) to somatic cells of mammals, the pre-treatment of the cells can also be carried out. For example, when adherent somatic cells are used, it can be preferable to pretreat the somatic cells to detach the cells from the cell supports (for example, culture dishes or cell culture supports).

The cell pretreatment in contacting 30S ribosomal protein includes, for example, digestive enzyme treatments, specifically, a trypsin treatment, or treatments with commercially available cell detachment solutions, for example, non-enzymatic cell detachment solutions, the trypsin treatment being possibly preferable.

The organism from which the 30S ribosomal protein to be used in the present invention is derived is not particularly limited. For example, Gram-positive bacteria, Gram-negative bacteria and fungi can be mentioned, although the organism is not limited thereto. Examples of gram-positive bacteria include lactic acid bacteria, staphylococci, closely related species of staphylococci, *Bacillus subtilis* (*Bacillus natto*) and the like. Examples of gram-negative bacteria include *Escherichia coli*, closely related species of *Pseudomonas aeruginosa* and root nodule bacteria (plant symbiotic bacteria). As fungi, for example, yeasts, mushrooms and molds can be described.

The somatic cell type used for induction of reprogramming or production of cells having pluripotency in the present invention is not particularly limited, and any somatic cells can be used. That is, the somatic cells as referred to in the present invention encompass all cells other than the germ cells among cells constituting the living organism, and may be differentiated somatic cells or undifferentiated stem cells having partially differentiated. They include, for example, but not limited to, epithelial cells, endothelial cells, fibroblasts (skin cells, etc.), intestinal cells, hepatocytes, splenocytes, pancreatic cells, renal cells, hair cells, muscle cells, brain cells, lung cells, adipocytes, differentiated cells such as gastric mucosal cells and the like, neural stem cells, hematopoietic stem cells, mesenchymal stem cells, somatic stem cells having partially differentiated such as dental pulp stem cells and the like, and tissue precursor cells. These cells are generally classified as adherent cells. The somatic cell origin is not particularly limited as long as it is a mammal, but is preferably a rodent such as a mouse, or a primate such as a human, particularly preferably a human or a mouse. When human somatic cells are used, any somatic cells of fetus, neonate or adult may be used.

When cells having pluripotency produced by the method according to the exemplary embodiments of the present disclosure can be used for treatments of diseases such as regenerative medicine, it is preferable to use somatic cells isolated from the patient itself suffering from the disease. In the exemplary embodiments of the present disclosure, cancer cells can be used as the cells. By bringing at least one 30S ribosomal protein selected from the group consisting of 30S ribosomal protein S2, 30S ribosomal protein S8 and 30S ribosomal protein S15 into contact with the cancer cells, non-cancer cells can be produced from the cancer cells. In the exemplary embodiments of the present disclosure, the procedure of bringing the 30S ribosomal protein into contact with somatic cells or cancer cells may be carried out in vitro or in vivo, and it can be conducted, e.g., in vitro.

The cell having pluripotency referred to in the exemplary embodiments of the present disclosure can mean a cell which has a self-replication ability under predetermined culture conditions and has a multipotential ability of differentiating into many kinds of cells (ectodermal cells, mesodermal cells, endodermal cells) under predetermined differentiation induction conditions (such cells are also referred to as stem cells).

The cells having pluripotency induced by the method according to the exemplary embodiments of the present disclosure can have a feature of having a self-replicating ability under predetermined culture conditions, but having no infinite proliferative property like iPS cells.

The cells having pluripotency induced by the method of the exemplary embodiments of the present disclosure can also have a feature that there is no difference from self cells and the risk of canceration is not increased by imparting pluripotency.

When producing the cells having pluripotency by bringing the 30S ribosomal protein into contact with somatic cells according to the exemplary embodiments of the present disclosure, it is possible to increase the cell cluster formation efficiency by bringing the ribosomal fraction into contact with somatic cells in the presence of methyl-β-cyclodextrin.

In the exemplary embodiments of the present disclosure, the cells having pluripotency or non-cancer cells (cells non-cancerized by reprogramming cancer cells) of the exemplary embodiments of the present disclosure can be produced by culturing somatic cells for 1 day or more, preferably several days or more (for example, 2 days or more or 3 days or more) in the presence of at least one 30S ribosomal protein selected from the group consisting of 30S ribosomal protein S2, 30S ribosomal protein S8 and 30S ribosomal protein S15 using a usual medium for cell culture, but the culture period is not limited to this. The upper limit of the culture period for producing and culturing cells having pluripotency is not particularly limited and can be appropriately selected depending on the purpose. Such media are not particularly limited, and it is possible to use any medium which can be used for culturing ES cells and iPS cells, and examples thereof include, but not limited to, Dulbecco's Modified Eagle medium (DMEM), Eagle minimal essential (EME) medium, Iscove's modified Dulbecco's medium (IMDM), alpha minimal essential medium (α-MEM), RPMI 1640, Ham-F-12, MCDB, and modified media thereof. The medium is preferably a serum-free medium from the viewpoint of the subsequent use and induction efficiency of the cells having pluripotency produced, and further, various growth factors, cytokines, hormones and the like, for example, components involved in proliferation and maintenance of human ES cells such as FGF-2, TGFβ-1, activin A, Noggin (Nanoggin), BDNF, NGF, NT-1, NT-2, NT-3 and the like may be added, if necessary. Such a medium containing 30S ribosomal protein is also a part of the present invention. The differentiation ability and proliferation ability of the isolated cells having pluripotency can be confirmed by utilizing a confirmation means known for ES cells.

At least one 30S ribosomal protein selected from the group consisting of 30S ribosomal protein S2, 30S ribosomal protein S8 and 30S ribosomal protein S15 used in the methods of the present invention may be any of a mixture simply extracted after expressing in a host such as *E. coli* and the like, a crudely purified material or a isolated and purified material, and though the protein is not particularly restricted as long as any of the above-described 30S ribosomes is contained, it is preferably a partially purified or purified material, further preferably a purified material. The concentration of the 30S ribosomal protein of the present invention to be added to the medium in culture is not particularly limited as long as the purpose of this invention is attained, and for example, the lower limit is 1 µg/mL or more, preferably 10 µg/mL or more, further preferably 50 µg/mL or more. The upper limit of the concentration can be selected without particular limitation as long as the concentration does not provide disadvantages for economical standpoint and the culture system.

Applications of cells having pluripotency and non-cancer cells produced by the method of the exemplary embodiments of the present disclosure are not limited, and they can be used for various tests and studies, treatments of diseases, and the like. For example, by treating a cell having pluripotency obtained by the method of the exemplary embodiments of the present disclosure with retinoic acid, a growth factor such as EGF, glucocorticoid or the like, a desired differentiated cell (for example, a neuronal cell, a cardiomyocyte, a hepatocyte, a pancreas cells, blood cells, etc.) can be induced, and by returning the differentiated cells thus obtained to the patient, stem cell therapy by autologous cell transplantation can be achieved.

Diseases of the central nervous system which can be treated using the cells having pluripotency of the exemplary embodiments of the present disclosure can include Parkinson's disease, Alzheimer's disease, multiple sclerosis, cerebral infarction, spinal cord injury and the like. For the treatment of Parkinson's disease, cells having pluripotency can be differentiated into dopaminergic neurons and transplanted into striatum of the Parkinson's disease patient. Differentiation into dopaminergic neurons can be progressed, for example, by co-culturing PA6 cells, the mouse stromal cell line, and cells having pluripotency of the exemplary embodiments of the present disclosure under serum-free conditions. In the treatment of Alzheimer's disease, cerebral infarction and spinal cord injury, the cells having pluripotency of the exemplary embodiments of the present disclosure can be differentiation-induced into neural stem cells before transplantation into the site of injury.

In addition, the cells having pluripotency of the exemplary embodiments of the present disclosure can be used for the treatment of liver diseases such as hepatitis, cirrhosis, liver failure and the like. To treat these diseases, the cells having pluripotency of the exemplary embodiments of the present disclosure can be differentiated into hepatocytes or hepatic stem cells, and then transplanted. A hepatocyte or a hepatic stem cell can be obtained by culturing the cell having pluripotency of the present invention in the presence of activin A for 5 days and then culturing for about 1 week with a hepatocyte growth factor (HIGF).

Furthermore, the cells having pluripotency of the present invention can be used for treating pancreatic diseases such as type I diabetes and the like. In the case of type I diabetes, the cells having pluripotency of the present invention can be differentiated into pancreatic β cells and transplanted into the pancreas. The exemplary method of differentiating the cells having pluripotency of the present invention into pancreatic β cells can be performed according to a method for differentiating ES cells into pancreatic β cells.

Furthermore, the cells having pluripotency of the exemplary embodiments of the present disclosure can be used for treating heart failure associated with ischemic heart disease. For the treatment of heart failure, it is preferable to differentiate the cells having pluripotency of the exemplary embodiments of the present disclosure into cardiomyocytes, then, transplant the cells to the site of injury. From the cells having pluripotency of the exemplary embodiments of the present disclosure cardiomyocytes can be obtained in about 2 weeks after the formation of embryoid bodies by adding noggin to the medium from 3 days before the formation of embryoid bodies.

According to the exemplary embodiments of the present disclosure, by bringing at least one 30S ribosomal protein selected from the group consisting of 30S ribosomal protein S2, 30S ribosomal protein S8 and 30S ribosomal protein S15 into contact with cancer cells, non-cancer cells can be produced from the cancer cells. Accordingly, a composition containing the 30S ribosomal protein used in the exemplary embodiments of the present disclosure can be useful as an anticancer agent.

Further, the composition containing at least one 30S ribosomal protein selected from the group consisting of 30S ribosomal protein S2, 30S ribosomal protein S8 and 30S ribosomal protein S15 provided by the exemplary embodiments of the present disclosure can be used as additives to pharmaceuticals and cosmetics since the composition can reprogram differentiated cells and cells having differentiated abnormally such as cancer cells.

When used as a medicament, it is administered to a patient together with a pharmaceutically acceptable carrier. The composition used as a medicament can further contain a stabilizer, a preservative, an isotonizing agent and the like. The method for administering the pharmaceutical composition of the exemplary embodiments of the present disclosure is not limited, but it can be carried out by either local administration or non-local administration. For local administration, it can be administered directly by means such as a syringe and the like. In the case of non-local administration, for example, it can be carried out intravenously.

The the exemplary embodiments of the present disclosure are specifically described herein by the following examples, and it should be understood that the exemplary embodiments of the present disclosure are not limited to the following examples.

EXAMPLES

Example 1: Measurement of Cell Reprogramming Activity

Measurement of cell reprogramming activity was carried out by measuring the cell cluster formation activity.

In a 10 cm petri dish, HDF cells (Human Dermal Fibroblasts, CELL APPLICATIONS INC, Cat No. 106-05a) were cultured with Fibroblast Growth Medium (CELL APPLICATION INC.). The cells were washed with 10 mL of CMF (Ca2+Mg2+-free buffer), and 1 mL of a 0.1% trypsin solution (containing 1 mM EDTA) was added and spread on the entire. The cells were placed in a CO2 incubator (37° C.) for 5 minutes, then, 3 mL of a trypsin inhibitor solution (CELL APPLICATION INC.) was added and suspended, and the number of cells was counted. A test sample (5 or 20 µg) was placed in a 96-well plate in advance, and 5×104 cells were suspended in 100 µL of a medium and this was added. The cells were cultured at 37° C. in a 5% CO2 incubator. Several days after, formation of cell clusters were observed.

Example 2: Batch Purification of Various Ribosomal Proteins from Recombinant E. coli Strains expressing ribosomal protein genes were purchased from ASKA(-) library in which the entire genes of E. coli AGI strain are cloned to His-tag added vector of National bio-resources project NBRP E. coli strain (http://www.shigen.nig.ac.jp/ecoli/strain/), and 21 kinds of strains were subjected to the following experiment. Information on ribosomal protein genes cloned to each strain is shown in the following table.

TABLE 1

| NBPR No. | Gene No. |
|---|---|
| JW0894 | rpsA |
| JW0164 | rpsB |
| JW3276 | rpsC |
| JW3258 | rpsD |
| JW3265 | rpsE |
| JW4158 | rpsF |
| JW3303 | rpsG |
| JW3268 | rpsH |
| JW3199 | rpsI |
| JW3283 | rpsJ |
| JW3259 | rpsK |
| JW3304 | rpsL |
| JW3260 | rpsM |
| JW3269 | rpsN |
| JW3134 | rpsO |
| JW2590 | rpsP |
| JW3273 | rpsQ |
| JW4160 | rpsR |
| JW3278 | rpsS |
| JW0022 | rpsT |
| JW3037 | rpsU |

Protein expression was performed using 21 E. coli strains. Purification of the expressed protein from E. coli followed the method as indicated by NBRP. Actually, each E. coli was cultured in 100 mL of LB medium, IPTG was added at the final concentration of 1 mM in the growth phase, and culturing for 2 hours was carried out to induce protein synthesis. E. coli was harvested by centrifugation, then, suspended in 1 mL of PBS, melted by ultrasonic disruption, and the centrifuged supernatant was collected as a crudely purified sample. Then, a His-tag protein bond resin (complete resin; Roche) was added to the crude sample, and the protein was purified according to the method indicated by the manufacturer. The concentration of imidazole was 5 mM for the washing buffer and 250 mM for the elution buffer, and 1 mL of an eluted sample was obtained. The eluted sample was concentrated to 50 µL using an ultrafiltration membrane (3,000 MW Amicon ultra; Millipore). The protein concentration of each sample obtained was measured by Protein assay (Biorad).

Example 3: Measurement of Cell Cluster Formation Activity of Various Ribosomal Proteins The cell cluster formation activity was measured according to the method in Example 1, using various ribosomal protein samples obtained in Example 2. Specifically, for each sample, 5 µg of a protein was added to each well and the cell cluster formation activity was measured. The experiment was performed multiple times.

As a result, the cell cluster formation activity was observed in samples from JW0164 strain expressing a gene coding RpsB (30S ribosomal protein S2), JW3268 strain expressing a gene coding RpsH (30S ribosomal protein S8) and JW3134 strain expressing a gene coding RpsO (30S ribosomal protein S15). In contrast, no cell cluster was formed in samples from other strains.

Example 4: Large-Scale Expression of 30S Ribosomal Protein S2 (RpsB) and Purification at High Purity JW0164 (E. coli expressing RpsB) was cultured, and purified 30S ribosomal protein S2 was obtained as follows. The culture method was carried out in the same manner as in Example 2. Culture scale was adjusted to 1 L. After culturing, Escherichia coli were harvested and disrupted, and 30 mL of the supernatant was recovered. Next, complete resin column (1 mL) (Roche) was connected to the FPLC system (acta prime; GE healthcare), and the protein was purified under the following conditions.

Binding buffer: PBS; washing buffer: PBS+5 mM imidazole; elution buffer: PBS+250 mM imidazole, Fraction volume: 1 mL; Elution volume: 20 mL; total 20 tubes.

The protein concentration of each fraction was measured, and the highest concentration fraction was adjusted to 1 µg/µL. After addition of 20 µg of a protein to the well, the cell cluster formation activity was measured according to the method in Example 1.

As a result, the cell cluster forming ability of JW0164-rpsB observed in Example 3 could be reproduced as shown in FIG. 1.

Example 5: Cell Cluster Formation Using 30S Ribosomal Protein S8 (RpsH) and S15 (RpsO)

Figure 2:
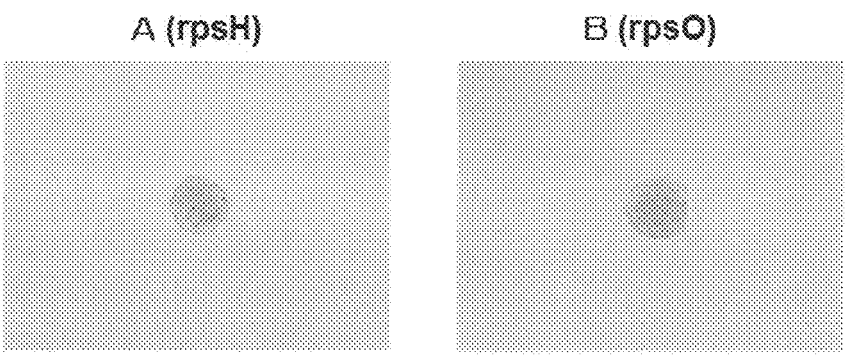
FIG. 2A is an illustration of HDF cells cultured together with the purified 30S ribosomal protein S8 or S15 prepared in Example 5, whereas a cell cluster is induced by the RpsH protein.
FIG. 2B is an illustration of HDF cells cultured together with the purified 30S ribosomal protein S8 or S15 prepared in Example 5, whereas a cell cluster is induced by the RpsO protein.

In the same manner as in Example 4, 30S ribosomal protein S8 (RpsH) and 30S ribosomal protein S15 (RpsO) were prepared using JW3268 (E. coli expressing RpsH) and JW3134 (E. coli expressing RpsO), and the cell cluster forming ability of them was measured. As a result, the cell cluster formation ability of JW3268-rpsH and JW3134-rpsO could be reproduced as shown in FIG. 2.

Example 6: Induction of Differentiation of Cell Clusters Formed

The present inventors have already reported that a 30S ribosome fraction derived from lactic acid bacteria purified from lactic acid bacteria lysate using sucrose concentration gradient ultracentrifugation has the cell cluster formation activity, and additionally, the cell clusters formed were differentiation-induced to adipocytes, osteocytes and chondrocytes (see, e.g., International Patent Application PCT/JP2015/063457). It has been confirmed that also cell clusters produced by using 30S ribosomal protein by the present invention is differentiation-induced to various cells as described below.

Cell clusters were produced using JW0164-rpsB protein, JW3268-rpsH protein and JW3134-rpsO protein. After two weeks, the culture medium was replaced with culture media (GIBCO; A 10072-01, A 10070-01, or A 10071-01) which promote differentiation-induction to adipocytes, osteoblasts and chondrocytes, and cultured further for 2 weeks.

Figure 3:
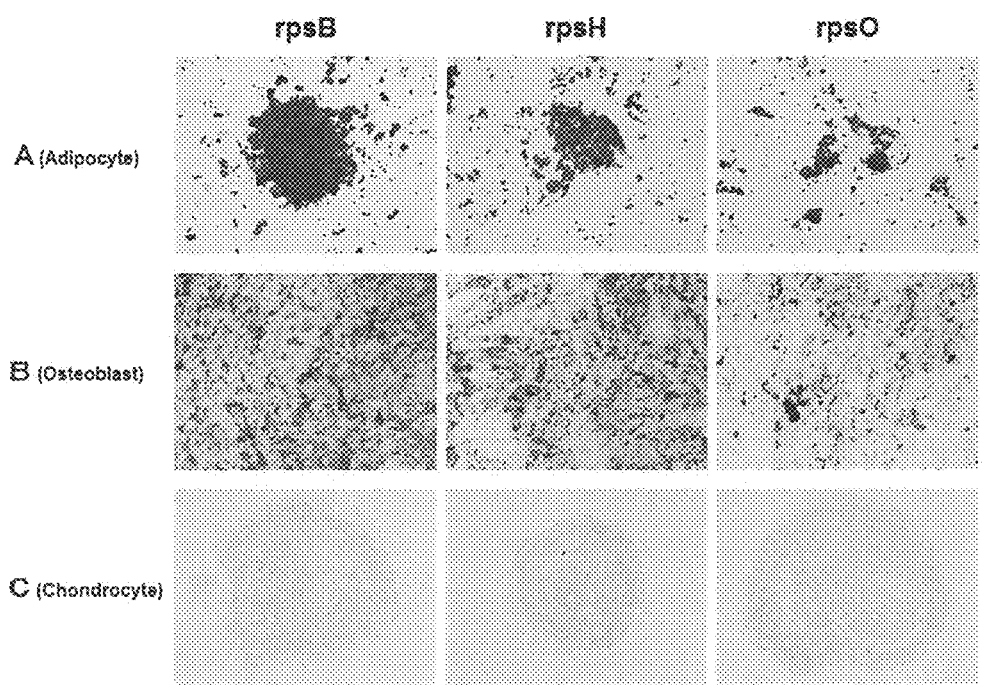
FIG. 3A is an illustration of the results of induction of differentiation into adipocytes of the cell clusters produced by culturing together with 30S ribosomal protein S2, S8 or S5.
FIG. 3B is an illustration of the results of induction of differentiation into osteoblasts of the cell clusters produced by culturing together with 30S ribosomal protein S2, S8 or S15.
FIG. 3C is an illustration of the results of induction of differentiation into chondrocytes of the cell clusters produced by culturing together with 30S ribosomal protein S2, S8 or S15.

As a result, the cell clusters produced by using each protein were stained by Oil Red O staining (adipocyte), Alizarin Red S staining (osteoblast) and Alcian Blue staining (chondrocyte), and differentiation of cells could be confirmed, as shown in FIG. 3.

The above-described description merely illustrates exemplary objects and subjects of the exemplary embodiments of the present disclosure, and does not limit the present disclosure. Without departing from the present disclosure, various modifications and alterations to the described exemplary embodiments will be apparent to those skilled in the art in view of the teachings herein.

The exemplary embodiments of the present disclosure can be useful as a composition for inducing somatic cell reprogramming and further as a method for producing cells having pluripotency from somatic cells. In addition, the composition and the method of the present invention are useful in medical fields (drug discovery research, examination of safety, efficacy and side effects of drugs), disease research (clarification of the cause of intractable diseases, development of therapeutic and preventive methods), regeneration medicine (restoration of function of nerve, blood vessel, organ), and food field.

The invention claimed is:

1. A method for inducing reprogramming of an isolated somatic cell obtained from a mammal, comprising:
   a) culturing the isolated somatic cell in a reprogramming medium containing at least one ribosomal protein selected from the group consisting of 30S ribosomal protein S2, 30S ribosomal protein S8 and 30S ribosomal protein S15,
   b) culturing the cell of step (a) for a period of time sufficient for the ribosomal protein S2, S8 and S15 to induce a ribosomal protein-induced cell cluster, wherein the cell cluster contains reprogrammed somatic cells expressing markers of pluripotency of ES cells or iPS cells, and
   c) measuring cell cluster formation activity by observing the cell cluster induced from the medium,
   wherein the 30S ribosomal proteins S2, S8 and S15 are isolated and purified from an *E. coli* strain expressing a gene coding RpsB protein, RpsH protein or RpsO protein, respectively,
   wherein the isolated somatic cell is a human fibroblast.

2. The method according to claim 1, wherein the at least one ribosomal protein is the 30S ribosomal protein S2.

3. The method according to claim 1, wherein the at least one ribosomal protein is the 30S ribosomal protein S8.

4. The method according to claim 1, wherein the at least one ribosomal protein is the 30S ribosomal protein S15.

5. The method according to claim 1, wherein said cell cluster is capable of differentiation-induction into adipocytes, osteocytes or chondrocytes.

* * * * *

SEQUENCE LISTING

```
<160> NUMBER OF SEQ ID NOS: 3

<210> SEQ ID NO 1
<211> LENGTH: 241
<212> TYPE: PRT
<213> ORGANISM: Escherichia coli

<400> SEQUENCE: 1

Met Ala Thr Val Ser Met Arg Asp Met Leu Lys Ala Gly Val His Phe
1               5                   10                  15

Gly His Gln Thr Arg Tyr Trp Asn Pro Lys Met Lys Pro Phe Ile Phe
            20                  25                  30

Gly Ala Arg Asn Lys Val His Ile Ile Asn Leu Glu Lys Thr Val Pro
        35                  40                  45

Met Phe Asn Glu Ala Leu Ala Glu Leu Asn Lys Ile Ala Ser Arg Lys
    50                  55                  60

Gly Lys Ile Leu Phe Val Gly Thr Lys Arg Ala Ala Ser Glu Ala Val
65                  70                  75                  80

Lys Asp Ala Ala Leu Ser Cys Asp Gln Phe Phe Val Asn His Arg Trp
                85                  90                  95

Leu Gly Gly Met Leu Thr Asn Trp Lys Thr Val Arg Gln Ser Ile Lys
            100                 105                 110

Arg Leu Lys Asp Leu Glu Thr Gln Ser Gln Asp Gly Thr Phe Asp Lys
        115                 120                 125

Leu Thr Lys Lys Glu Ala Leu Met Arg Thr Arg Glu Leu Glu Lys Leu
    130                 135                 140

Glu Asn Ser Leu Gly Gly Ile Lys Asp Met Gly Gly Leu Pro Asp Ala
145                 150                 155                 160

Leu Phe Val Ile Asp Ala Asp His Glu His Ile Ala Ile Lys Glu Ala
                165                 170                 175

Asn Asn Leu Gly Ile Pro Val Phe Ala Ile Val Asp Thr Asn Ser Asp
            180                 185                 190

Pro Asp Gly Val Asp Phe Val Ile Pro Gly Asn Asp Asp Ala Ile Arg
        195                 200                 205

Ala Val Thr Leu Tyr Leu Gly Ala Val Ala Ala Thr Val Arg Glu Gly
    210                 215                 220

Arg Ser Gln Asp Leu Ala Ser Gln Ala Glu Glu Ser Phe Val Glu Ala
225                 230                 235                 240

Glu

<210> SEQ ID NO 2
<211> LENGTH: 130
<212> TYPE: PRT
<213> ORGANISM: Escherichia coli

<400> SEQUENCE: 2

Met Ser Met Gln Asp Pro Ile Ala Asp Met Leu Thr Arg Ile Arg Asn
1               5                   10                  15
```

-continued

```
Gly Gln Ala Ala Asn Lys Ala Ala Val Thr Met Pro Ser Ser Lys Leu
            20                  25                  30

Lys Val Ala Ile Ala Asn Val Leu Lys Glu Glu Gly Phe Ile Glu Asp
            35                  40                  45

Phe Lys Val Glu Gly Asp Thr Lys Pro Glu Leu Glu Leu Thr Leu Lys
        50                  55                  60

Tyr Phe Gln Gly Lys Ala Val Val Glu Ser Ile Gln Arg Val Ser Arg
65                  70                  75                  80

Pro Gly Leu Arg Ile Tyr Lys Arg Lys Asp Glu Leu Pro Lys Val Met
                85                  90                  95

Ala Gly Leu Gly Ile Ala Val Val Ser Thr Ser Lys Gly Val Met Thr
                100                 105                 110

Asp Arg Ala Ala Arg Gln Ala Gly Leu Gly Gly Glu Ile Ile Cys Tyr
            115                 120                 125

Val Ala
    130

<210> SEQ ID NO 3
<211> LENGTH: 89
<212> TYPE: PRT
<213> ORGANISM: Escherichia coli

<400> SEQUENCE: 3

Met Ser Leu Ser Thr Glu Ala Thr Ala Lys Ile Val Ser Glu Phe Gly
1               5                   10                  15

Arg Asp Ala Asn Asp Thr Gly Ser Thr Glu Val Gln Val Ala Leu Leu
            20                  25                  30

Thr Ala Gln Ile Asn His Leu Gln Gly His Phe Ala Glu His Lys Lys
        35                  40                  45

Asp His His Ser Arg Arg Gly Leu Leu Arg Met Val Ser Gln Arg Arg
    50                  55                  60

Lys Leu Leu Asp Tyr Leu Lys Arg Lys Asp Val Ala Arg Tyr Thr Gln
65                  70                  75                  80

Leu Ile Glu Arg Leu Gly Leu Arg Arg
                85
```